United States Patent [19]

Holtkamp

[11] Plant 4,497

[45] Jan. 29, 1980

[54] AFRICAN VIOLET PLANT

[75] Inventor: Reinhold Holtkamp, Isselburg, Fed. Rep. of Germany

[73] Assignee: Gessellschaftsvertrag uber die Erfindergemeinschaft "OPTIMARA", Isselburg, Fed. Rep. of Germany

[21] Appl. No.: 966,224

[22] Filed: Dec. 4, 1978

[51] Int. Cl.[2] ..... A01H 5/00

[52] U.S. Cl. ..... Plt./69

[58] Field of Search ..... Plt./69

*Primary Examiner*—Robert E. Bagwill
*Attorney, Agent, or Firm*—Donald D. Jeffery

[57] ABSTRACT

An African violet plant known by the cultivar name Missouri and particularly characterized by the combined features of vigorous and compact growth habit; intensive red-violet flowers with frilled edges; strong and upright flower stems; long blooming period, and an abundant flower display at first flash.

1 Drawing Figure

The present invention comprises a new and distinct cultivar of African violet plant, botanically known as *Saintpaulia ionantha,* and hereinafter referred to by the cultivar name Missouri. The new cultivar, identified during the breeding and selection process by the designation b. 17/11-66/78 red frilled, is a product of a planned breeding program of the present inventor. Missouri is characterized principally by its frilled flower edges, red-violet flower color, very strong and upright flower stems, compact habit, and non-dropping flowers. These traits in combination were not present in previously available commercial African violet cultivars.

The new cultivar was originated from a cross made in a controlled breeding program in Isselburg, Rhineland, Germany. The female, or seed parent was F III (color: RHS 62-D), an unpatented cultivar. The male, or pollen parent was XIX 4001 red (color RHS 71-A), likewise an unpatented cultivar.

The new cultivar Missouri was discovered and selected as a flowering plant within the progeny of the stated cross by me in a controlled environment in Isselburg, Rhineland, Germany.

Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of Missouri, which in combination distinguish this African violet as a new and distinct cultivar:

(1) Compact habit.

(2) Vigorous growth with upright flower stems, which are very strong.

(3) Long blooming period.

(4) Rich in flowers, with the flowers having frilled edges and being non-dropping.

(5) The plant is attractive and saleable with the first flash of flowers.

(6) Intensive red-violet flower color.

The accompanying photographic drawing shows a typical specimen plant of the new cultivar. The colors appearing in the photograph are as true as possible with color illustrations of this type.

In the following description, color references are made to the Royal Horticultural Society (RHS), color chart, except where general color terms of ordinary significance are obvious.

Botanical classification: *Saintpaulia ionantha,* Ramat, cv Missouri

Parentage:

*Male Parent.*—XIX 4001, Color RHS 71-A.

*Female Parent.*—F III, Color RHS 62-D.

Propagation: The new cultivar holds its distinguishing characteristics through successive propagations by leaf cuttings and by division of shoots.

Plant: From 7 cm. to 9 cm. tall when grown in pots, and approximately 23 cm. in diameter when fully grown.

*Leaves.*—General Form: oval to round. Diameter: 50–55 mm. Texture: soft, hairy. Aspect: velvety. Veins: well pronounced on underside. Color (upperside): 131A. Color (underside): uneven; red brown to green. Petiole: light red-brown.

Flowers:

*Buds.*—Ball-shaped; 6–7 mm. in diameter, color 73-C.

*Sepals.*—Spear-shaped. Color: RHS 59B. Calyx: funnel-shaped. Aspect: flat-funnel. Peduncle: upright and strong.

Individual flowers:

*Size.*—35–40 mm. in diameter.

*Color.*—Upperside: 72 A-B. Underside: 72C.

*Borne.*—Up to 8 flowers per stem.

*Shape.*—Five; two small, 3 large, all frilled; small, 17 mm. long, 12 mm. wide; large 22 mm. long, 17 mm. wide.

*Arrangement.*—Upright and strong peduncle, with up to 8 flowers.

*Flowering time.*—8–9 weeks after potting the first flowers appear, and plant is in full flower in two more weeks.

Reproductive organs:

*Stamens.*—Two, color 7B.

*Anthers.*—Four, color 7B; capsule pushes slightly through.

*Arrangement.*—Basifixed.

*Filaments.*—3–4 mm. long, greenish, reddish on base.

*Styles.*—Reddish violet, connected to seed capsule.

*Pollen color.*—Very fine, color 7-C.

Roots: White when young and active.

Disease Resistance: Very good.

General observations: Missouri is a vigorous grower. The flowers are carried on strong upright stems, and the bouquet is centrally above the foliage. The frilled edge, red-violet flowers are plentiful, and 7–9 flowers appear in the first flash, thereby making the plant highly saleable.

I claim:

1. A new and distinct cultivar of African violet plant known by the cultivar name Missouri and particularly characterized by the combined features of vigorous and compact growth habit; intensive red-violet flowers with filled edges; strong and upright flower stems; long blooming period, and an abundant flower display at first flash.

* * * * *

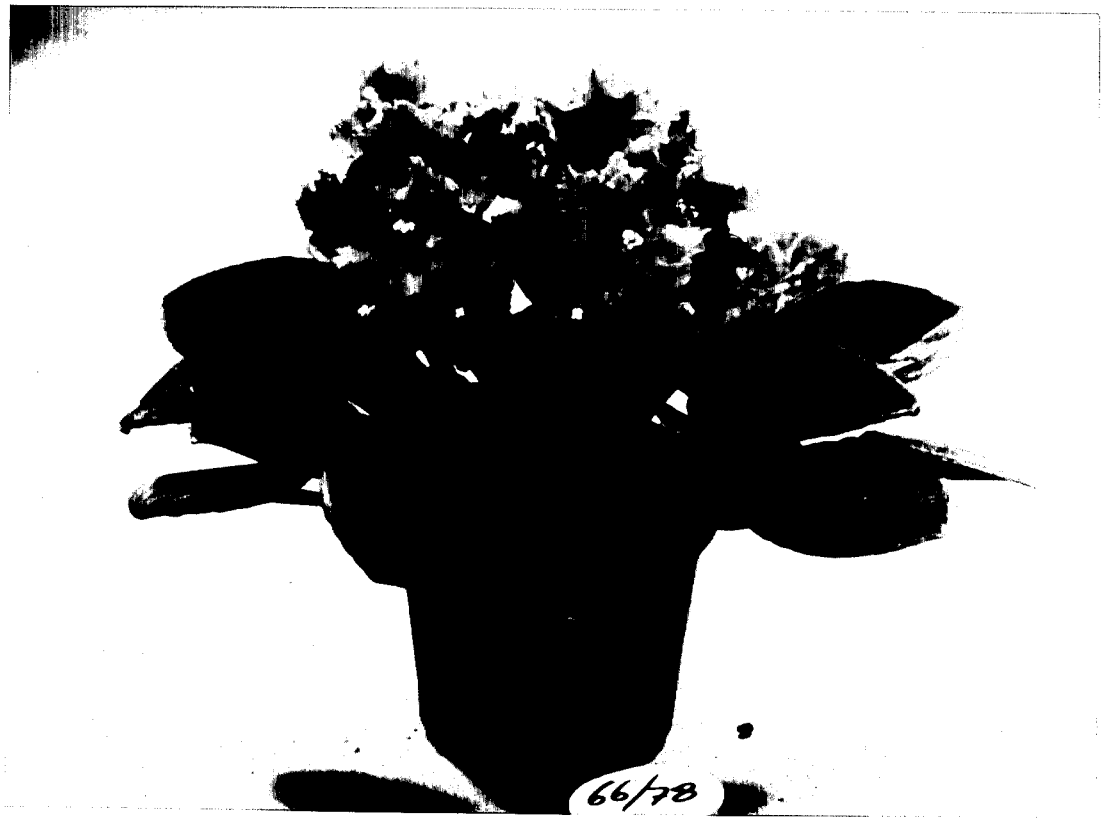
66/78